(12) United States Patent
Liebers

(10) Patent No.: US 6,257,724 B1
(45) Date of Patent: Jul. 10, 2001

(54) TESTER FOR NEAR VISION

(75) Inventor: Steven B. Liebers, Norristown, PA (US)

(73) Assignee: Diversified Products, Inc., Norristown, PA (US)

( * ) Notice: Subject to any disclaimer, the term of this patent is extended or adjusted under 35 U.S.C. 154(b) by 0 days.

(21) Appl. No.: 09/629,760

(22) Filed: Jul. 31, 2000

(51) Int. Cl.[7] ........................................ A61B 3/02
(52) U.S. Cl. ............................................. 351/245
(58) Field of Search ................... 351/222, 223, 351/227, 229, 233, 234, 235, 243, 245; 345/7; 211/166

(56) References Cited

U.S. PATENT DOCUMENTS

| | | |
|---|---|---|
| 1,228,020 | 5/1917 | Herrick . |
| 1,284,103 | 11/1918 | Herrick . |
| 1,384,252 | 7/1921 | Giddens . |
| 1,416,159 | 5/1922 | Barr . |
| 1,437,776 | 12/1922 | Reese et al. . |
| 4,896,959 | 1/1990 | O'Brien . |
| 5,257,703 | * 11/1993 | Ascik et al. ..................... 211/166 |
| 5,486,879 | 1/1996 | Barnett . |
| 5,861,941 | 1/1999 | Liebers . |
| 6,005,536 | * 12/1999 | Beadles et al. ..................... 345/7 |

FOREIGN PATENT DOCUMENTS

| | | |
|---|---|---|
| 2293023 | 3/1996 | (GB) . |
| WO 95/19133 | 7/1995 | (WO) . |

* cited by examiner

Primary Examiner—George Manuel
(74) Attorney, Agent, or Firm—Caesar, Rivise, Bernstein, Cohen & Pokotilow, Ltd.

(57) ABSTRACT

A vision tester comprising a front wall and a top. The top has positioned thereon printed matter. The front wall has at least one opening through which the user of the vision tester looks. A plurality of magnifying lenses, of different diopter ratings, are selectively positionable behind the opening. Indicia appear to indicate the diopter rating of each lens. A mirror, at an obtuse angle, is positioned behind the opening and below the top of the vision tester. The user of the vision tester can determine the diopter rating of the appropriate lens needed for reading by determining which lens renders the printed matter clear and readable, and noting the appropriate rating.

20 Claims, 5 Drawing Sheets

TESTER FOR NEAR VISION

BACKGROUND OF THE INVENTION

This invention relates to a vision tester, in general, and, more particularly, to a device for use by a consumer in testing his near vision to determine the strength of non-prescription reading glasses the consumer requires.

It is now a common practice to sell non-prescription reading glasses directly to the consumer at pharmacies and other retail outlets. The non-prescription reading glasses are displayed in a retail establishment on free-standing displays.

Typically, a consumer selects a pair of non-prescription reading glasses from the display by trying on a number of pairs until he locates a pair that is suitable, from the standpoint of comfort, magnifying ability and appearance. In order to determine the appropriate magnifying ability for the reading glasses, charts are placed on the displays for the reading glasses. The charts have increasing sizes of print, and the purchaser of the reading glasses is instructed to stand approximately 14 inches (35.6 cm.) from the chart. When viewing the chart, the consumer will look at each line of print, and note the first line of print that appears to be out of focus. By reading across the chart, the consumer can then determine the amount of magnification needed for the reading glasses. The amount is expressed in diopters, an optical unit of measurement.

Once the consumer determines the appropriate amount of magnification needed, the consumer will then view all of the glasses on the display rack that have lenses at the appropriate diopter rating. The consumer can then select a pair of reading glasses which the consumer finds to be attractive and comfortable.

Although the use of the charts can effectively determine the proper amount of magnification needed for the reading glasses, it has been found that the use of the charts is imprecise. Quite often, the consumer will not stand an appropriate distance from the chart and, accordingly, consumers test the reading glasses by simply trying on a large number of reading glasses, of different magnifications, and testing them in connection with reading matter that is hand held by the consumer. The consumer will not always replace the reading glasses that have been tried on in the proper place on the display rack, and eventually, the reading glasses on the display rack are in total disarray.

A vision tester that has overcome the foregoing problems is disclosed in U.S. Pat. No. 5,861,941, the disclosure of which is incorporated by reference herein. Applicant is one of the co-inventors of the invention disclosed in that patent.

The device disclosed in U.S. Pat. No. 5,861,941 precisely measures the magnification power necessary for the reading glasses of each consumer. By utilizing the device, the consumer can accurately determine the appropriate diopter rating for the reading glasses, and try on only those reading glasses having that diopter rating. Since the reading glasses will be removed from only one segment of the display holding reading glasses, there is a much greater probability that the reading glasses will be returned to that segment after they are tried on, if they are not purchased.

Another advantage of the prior invention is that it is formed as part of a display rack for non-prescription reading glasses. This permits the consumer to test her vision at the same location as the location of the non-prescription reading glasses. Since the vision tester is formed as part of the display rack, there is little likelihood of damage caused by dropping or mishandling the vision tester.

The device of the instant invention enjoys all of the advantages of the invention covered by the prior patent. However, it also enjoys certain advantages over the prior invention.

In the prior invention, the distance between the reading material and the lenses used to test the near vision of the consumer was approximately 14 inches (35.6 cm.). That distance could easily be accommodated on a large display rack, such as the type shown in U.S. Pat. No. 5,861,941. However, in certain low-volume stores or in stores that do not have the floor space readily available to accommodate a large display rack, a smaller display rack that is placeable at the end of shelving is used. The smaller display rack can have a depth that is significantly less than 14 inches (35.6 cm.). The vision tester of the instant invention can be effectively used on display racks that have a depth that is significantly smaller than 14 inches (35.6 cm.).

Another advantage of the instant invention is that the light in the ceiling of a store projects directly on the printed material used for testing the vision. In the device covered by U.S. Pat. No. 5,861,941, ceiling light illuminated the printed material only indirectly, that is, the ceiling light projected downwardly and parallel to the printed material. Accordingly, in the instant invention, greater illumination of the printed material is obtained.

A third advantage of the instant invention is that the ceiling light, in passing through the printed material, strikes a mirror that is placed at an obtuse angle within the tester. The light from the ceiling strikes the mirror and passes through the eye holes containing the lenses for testing vision. The light projecting through the eye holes is visible to consumers walking by the display, and tends to attract consumers to the display.

SUMMARY OF THE INVENTION

A vision tester comprising a front wall and a top. The top has positioned thereon printed matter. The front wall has at least one opening through which the user of the vision tester looks. A plurality of magnifying lenses, of different diopter ratings, are selectively positionable behind the opening. Indicia appear to indicate the diopter rating of each lens. A mirror, at an obtuse angle, is positioned behind the opening and below the top of the vision tester. The user of the vision tester can determine the diopter rating of the appropriate lens needed for reading by determining which lens renders the printed matter clear and readable, and noting the appropriate rating.

DESCRIPTION OF THE DRAWINGS

Objects and many of the attendant advantages of this invention will become readily appreciated as the same becomes better understood by reference to the following detailed description, when considered in connection with the accompanying drawing, wherein.

DETAILED DESCRIPTION OF THE PREFERRED EMBODIMENT

Figure 1:
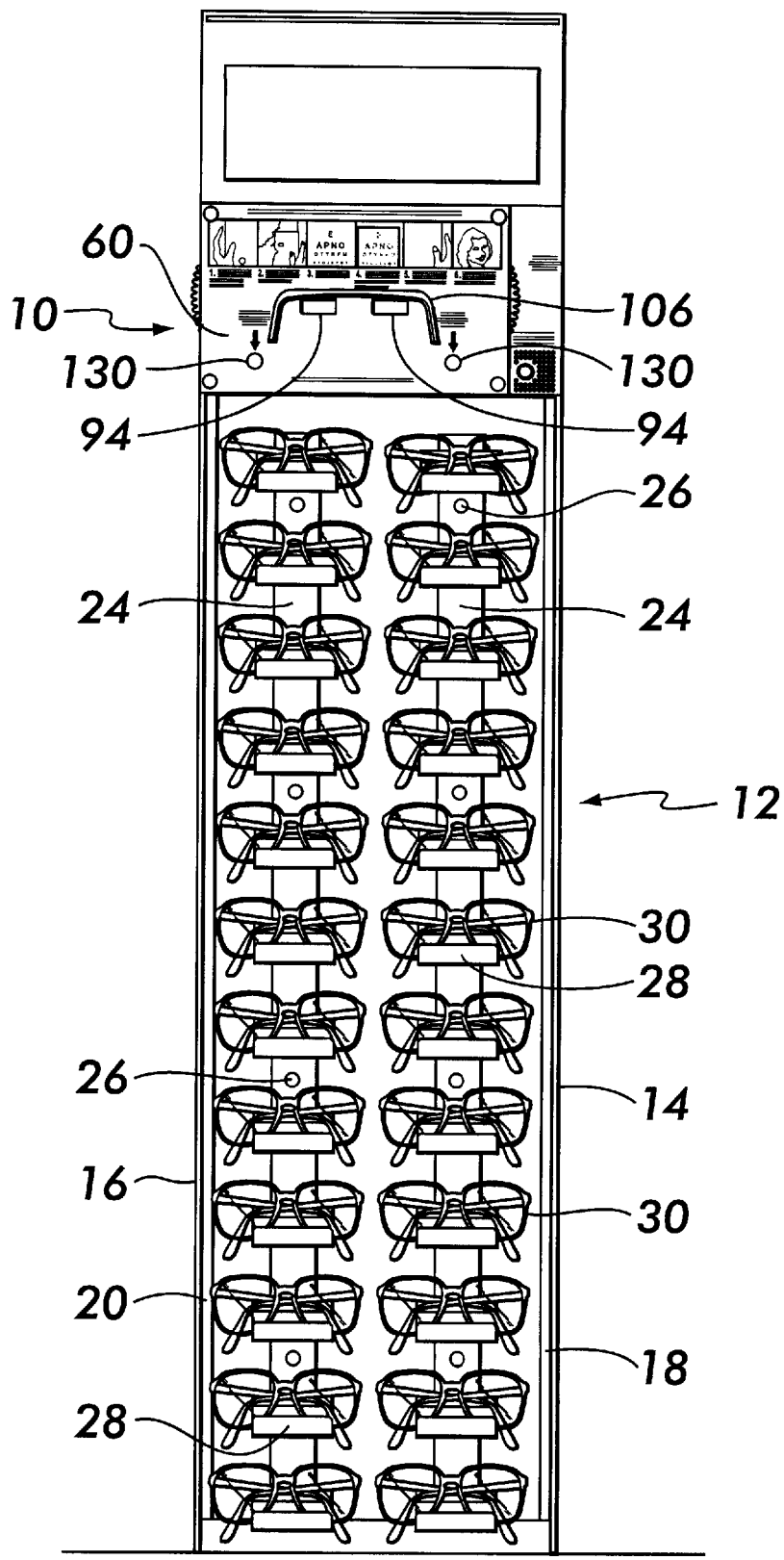
FIG. 1 is a front elevational view of an eyeglass display rack which incorporates the vision tester of this invention.

Referring now in greater detail to the various figures of the drawing, wherein like reference characters refer to like parts, a vision tester embodying the present invention is generally shown at 10 in FIG. 1. The vision tester 10 is mounted on a non-prescription reading glass display rack 12.

Figure 3:
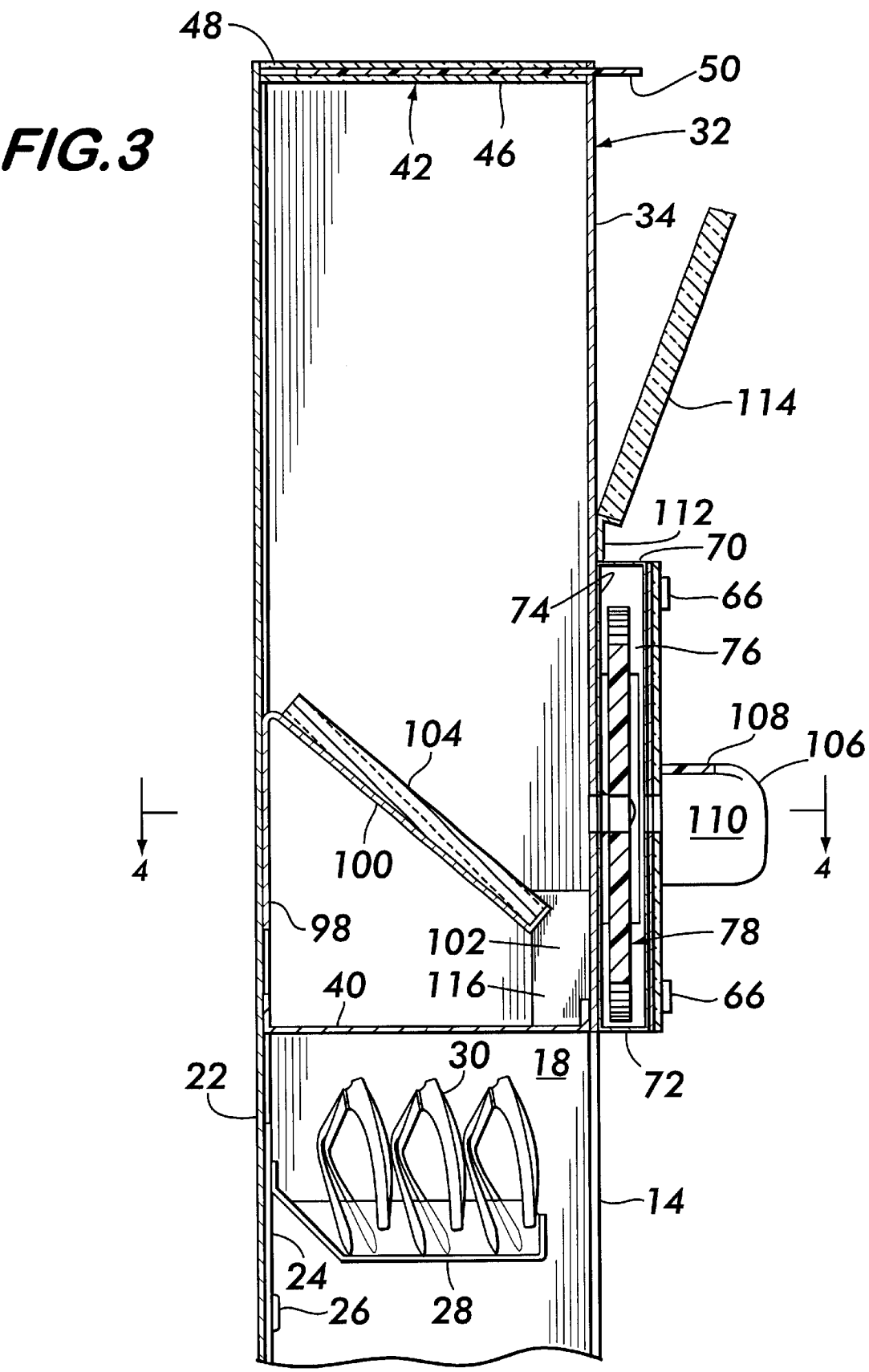
FIG. 3 is a sectional view taken along the line 3—3 of FIG. 2.

Referring to FIGS. 1 and 3, the display rack 12 includes a pair of side walls 14 and 16. Side walls 14 and 16 contain decorative or instructional materials relating to the display rack. Mounted within the side walls 14 and 16 are interior side walls 18 and 20.

As seen in FIG. 3, display rack 12 includes a rear wall 22. A pair of spaced vertically extending bars 24 are secured to the rear wall 22 by fasteners 26. A plurality of eyeglass-supporting trays 28 are secured to bars 24. Non-prescription eyeglasses 30 are placed on trays 28 for selection by a consumer.

The details of the supporting trays 28 and their function are described in co-pending application Ser. No. 09/492,972, filed on Jan. 27, 2000 and entitled "Eyeglass Display Rack and Tray Therefor," the disclosure of which is incorporated by reference herein. The display rack shown in the drawing and described in the aforementioned co-pending application is merely exemplary of the many display racks available for displaying and vending non-prescription reading glasses. The actual structure of the display rack does not form a part of this invention. Other racks and supports for the non-prescription reading -glasses can be used in carrying out this invention, such as those disclosed in U.S. Pat. Nos. 4,976,32, 5,100,006 and 5,861,941.

The novelty of this invention resides in the vision tester 10. The vision tester can be secured as an integral part of the display rack shown in the drawing, or as an integral part of any other display rack known to the art. It can also be placed on a support separate from a display rack.

The vision tester 10 comprises a housing 32 secured on rear wall 22 (FIG. 3). Housing 32 includes a front wall 34, side walls 36 an 38 (FIG. 4), a bottom wall 40 and a top 42. The side walls 36 and 38 are secured to the rear wall 22 of the display rack through flanges 44, which can be glued or welded to the rear wall 22.

The top 42 comprises a lower plate 46 (FIG. 3) and an upper plate 48. The two plates are parallel and are spaced apart. The plates are made from a transparent or translucent material, which can be glass or plastic.

A removable sheet 50 is positioned between plates 46 and 48. The sheet 50 has material printed thereon, which material is used in testing the near vision of the consumer.

Figure 5:
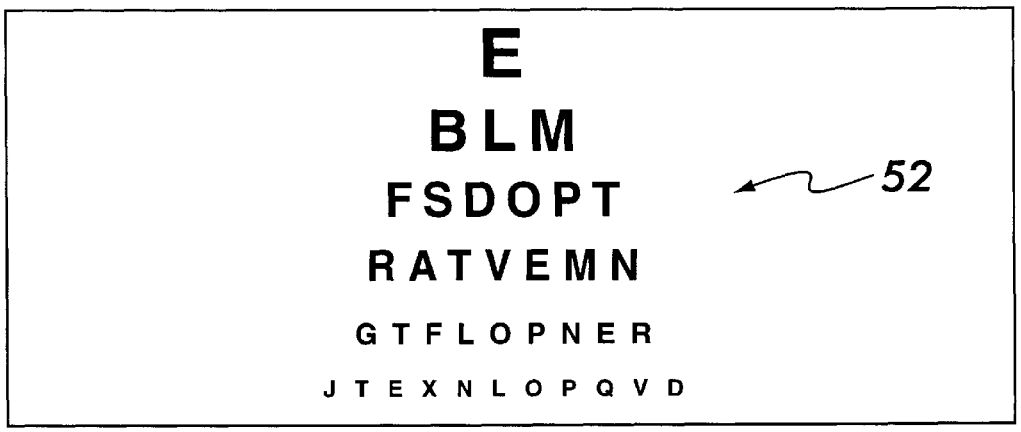
FIG. 5 is an elevational view of a first form of printed matter usable in this invention.

A first embodiment of the printed material that can be used on sheet 50 appears at 52 in FIG. 5. In this embodiment, the printed material appears as a conventional eye chart used by optometrists and ophthalmologists.

Figure 6:
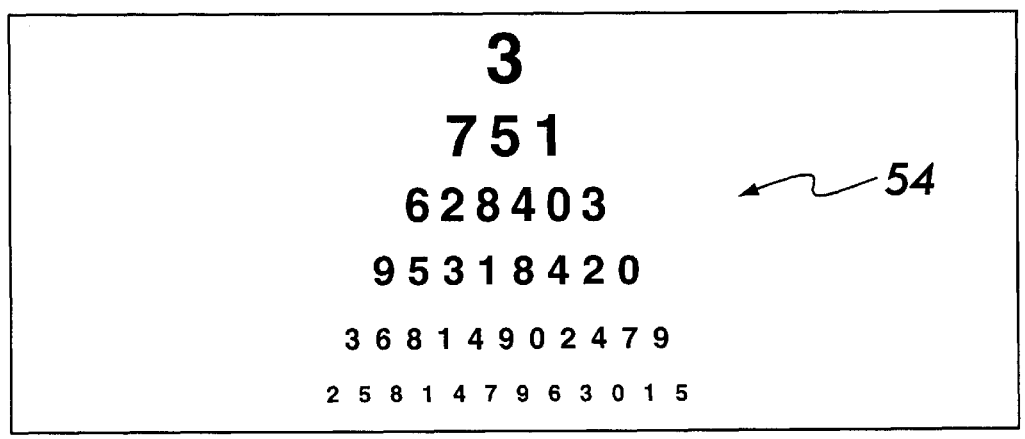
FIG. 6 is an elevational view of a second form of printed matter usable in this invention.

A second embodiment of the printed material is shown at 54 in FIG. 6. In this embodiment, the printed material appears as spaced lines of numbers, with the numbers decreasing in size in going from top to bottom.

Figure 7:
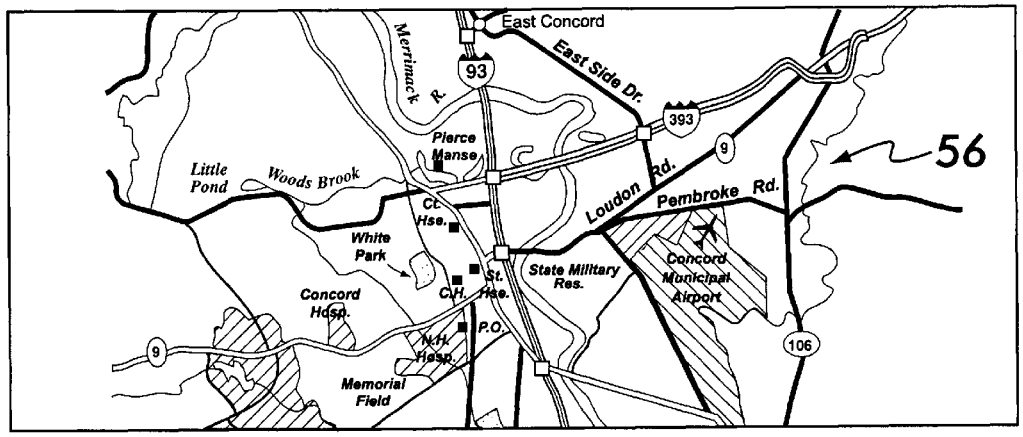
FIG. 7 is an elevational view of a third form of printed matter usable in this invention; and, FIG. 8 is an elevational view of one of the discs containing different lenses, usable in this invention.

A third embodiment of the printed material is shown at 56 in FIG. 7. In this embodiment, a segment of a map is used.

The printed material can take any form, and the exact form is not critical to this invention. The critical feature is that the printed material be capable of being viewed by the consumer, and that it be of sufficiently small print to enable the consumer to test his near vision. Instead of the embodiments shown in FIGS. 5, 6 and 7, the printed material can be English language words, and the size of the print for all of the words will be the same. In this way, the consumer will not have to test her vision with respect to different sizes of letters or numbers, when selecting the appropriate magnification for her reading glasses.

The sheet 50 can be removed and replaced simply by pulling on the forward end shown in FIG. 3. If it is desired to change the form of printed material, the sheet can be removed and a new sheet can be inserted. The sheet can be a transparent or translucent plastic having the numbers, letters, map, etc. printed thereon or it can even be a sheet of paper having the material printed thereon. Sufficient light will pass through the plates 46 and 48 to be able to read the material, even if it is printed on paper.

Figure 4:
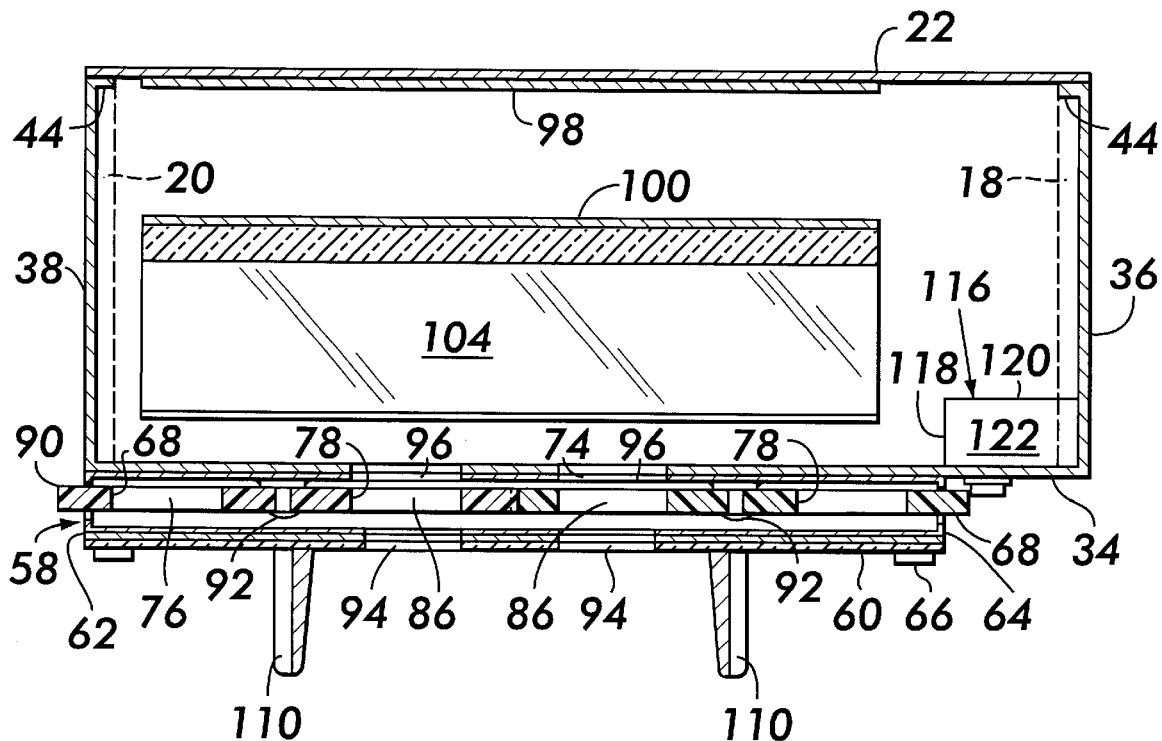
FIG. 4 is a sectional view taken along the line 4—4 of FIG. 3.

The front of vision tester 10 includes a lens housing 58. As seen in FIG. 4, lens housing 58 includes an outer plate 60, an intermediate plate 62 and an inner plate 64. Plates 60 and 62 are secured to plate 64 by pins 66. Plate 64 has side extensions 68, top extension 70 and bottom extension 72. As seen in FIG. 3, a rear wall 74, parallel to plate 64, is secured on front wall 32. As seen in FIGS. 3 and 4, a housing 76 is formed in the area bounded by plate 64, side extension 68, top extension 70, bottom extension 72 and rear wall 74.

Figure 2:
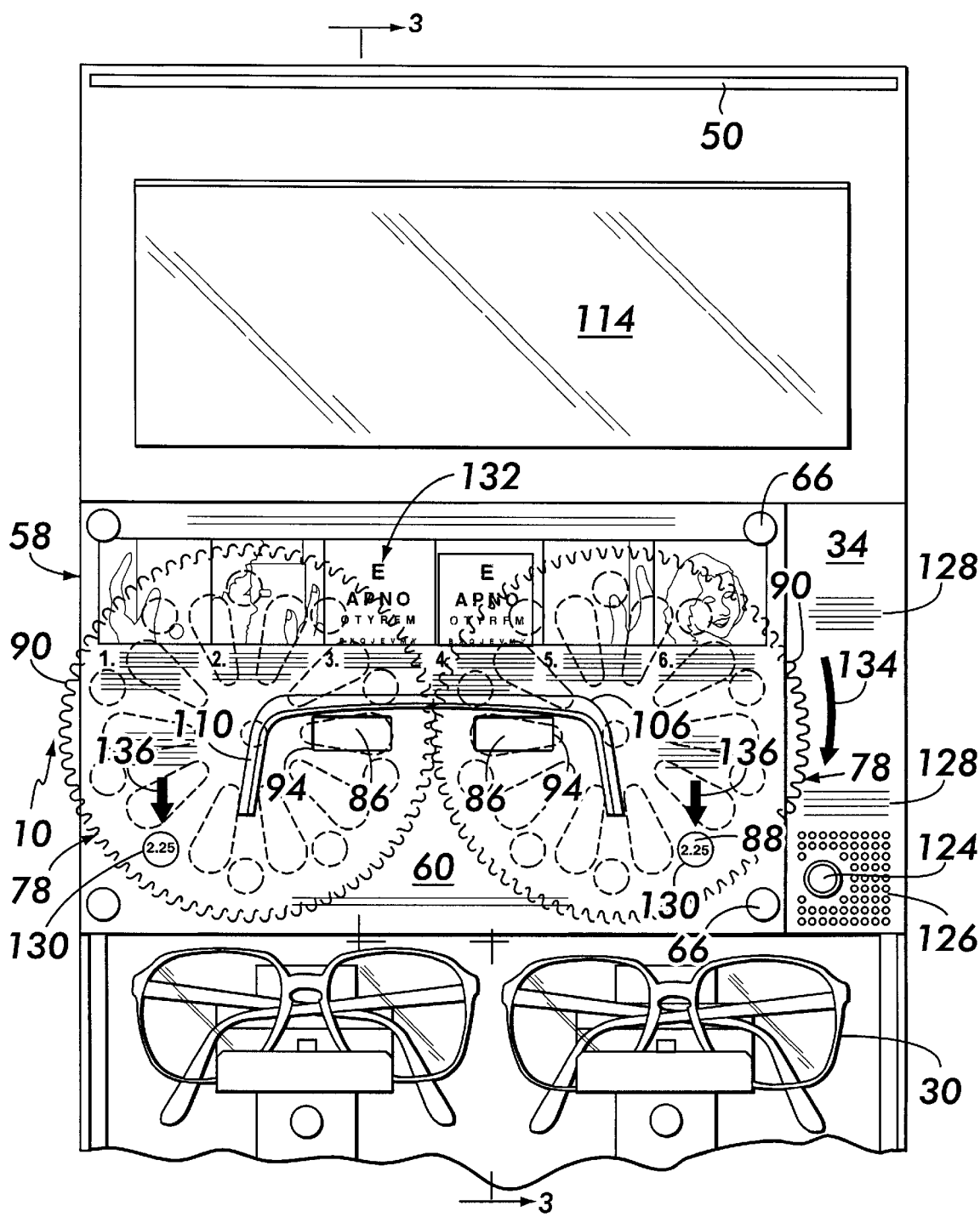
FIG. 2 is an enlarged elevational view of the top of the display rack of FIG. 1, showing the vision tester in greater detail.
Figure 8:
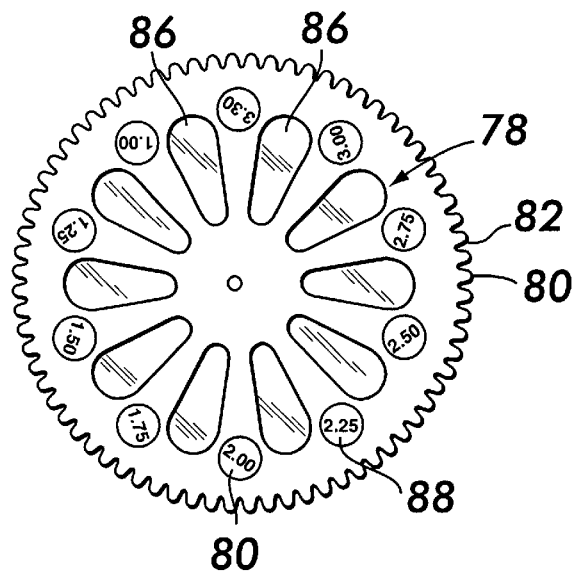

Rotatably mounted within housing 76 are a pair of discs 78 (FIG. 2). As best seen in FIG. 8, each disc 78 contains a plurality of equally-spaced teeth 80 extending around its entire circumference. Teeth 80 are separated by equally-spaced openings 82. A central opening 84 is formed in each disc 78. Each disc 78 includes a plurality of equally-spaced radially-extending openings in which are secured lenses 86. Each lens 86 is of a different magnification and, accordingly, has a different diopter rating. The diopter rating is a rating commonly used in optometry in describing the magnification power of a lens. The diopter ratings for the lenses are printed between the lenses, as shown at 88 in FIG. 3.

Referring to FIGS. 2 and 3, it is seen that discs 78 are aligned within housing 76. A tooth 80 of one disc is received in an opening 82 of the other disc. A portion 90 of each disc passes through a slot formed in an adjacent side extension 68. Discs 78 are rotatably mounted within housing 76 around pins 92 (FIG. 4) which pass through openings 84 of each disc.

A pair of spaced openings 94 are formed in aligned walls 60, 62 and 64. Positioned behind the openings 94 are lenses 86 of discs 78. Positioned behind the lenses are aligned openings 96 in walls 34 and 74.

As seen in FIG. 3, a plate 98 is secured on rear wall 22. Plate 98 has an upper bend, with plate 100 projecting downwardly, at an angle of approximately 135°, measured from a horizontal plane. Plate 100 has a lower flange 102 projecting upwardly and perpendicularly therefrom. A mirror 104 is secured to plate 100 and rests against flange 102.

An eye shield 106 is mounted on wall 60, and includes an upper member 108 and side members 110 projecting downwardly therefrom. The eye shield is positioned above and beside openings 94 (FIG. 2).

As seen in FIG. 3, a bracket 112 is mounted on front wall 34. A mirror 114 is secured to bracket 112, and projects at an angle of approximately 60°.

A chamber 116 (FIG. 3) is formed in housing 32. The chamber includes a side wall 118 (FIG. 4), a rear wall 120 and a top 122. The chamber walls are secured to side wall 36 and front wall 34 of housing 32.

Mounted within the chamber is a device (not shown) for playing a recorded message. As seen in FIG. 2, a pushbutton 124 projects through an opening in wall 34. The pushbutton will actuate the prerecorded message contained in the playback device mounted within chamber 114. A plurality of openings 126 are formed in wall 34 to permit the speaker of the playback device to project the sound from the playback device to the consumer. Printed instructional material 128 is placed above the speaker openings 126.

The playback device can be an integrated circuit voice synthesizer or any other solid state voice playback device. It can also be a magnetic tape recorder.

As seen in FIGS. 1 and 2, front wall 60 includes aligned openings 130. Diopter ratings 88 (FIG. 8) are visible through the openings. The diopter ratings correspond to the lens 86 appearing behind opening 94 (FIG. 2).

Instructions for use of the vision tester 10 are shown schematically at 132 in FIG. 2. The instructions can include photographs and descriptive words for determining the appropriate magnification for the nonprescription glasses, utilizing the device 10. Instructions can also be obtained by depressing pushbutton 124 and listening to the prerecorded message describing the use of the device.

The vision tester 10 is used by the consumer's standing in front of the display rack 12 and placing his eyes adjacent openings 94. The consumer's eyes are shielded from ambient light by eye shield 106.

The consumer will then look through openings 94, through a pair of aligned lenses 86, and through openings 96, to focus on mirror 104. Light from above the vision tester will pass through the printed material 50 at the top of the vision tester, and the image of the printed material will appear on the mirror 104. Accordingly, by focusing on the mirror, and through reflection from the mirror, the consumer will be able to view the printed material.

As previously pointed out, in testing non-prescription reading glasses, the object being viewed by the consumer should optimally be 14 inches (35.6 cm.) from the consumer's eyes. Assuming the center of the mirror, on which the consumer's eyes will be focused, is four inches (10.2 cm.) from the openings 94, then the distance from the center of the mirror to the printed sheet 50 should be 10 inches (25.4 cm.). In this way, the effective distance from the eye to the printed material will be 14 inches (35.6 cm.), although the depth of the vision tester need be less than five inches (12.7 cm.).

Once the printed material is viewed by the consumer, he then rotates one of the discs 78. This automatically rotates the other disc 78, by the engagement of the teeth 80 in the openings 82 of the corresponding disc. Rotation is accomplished by moving the exposed portion of one of the discs 78 (FIG. 2) around pins 92. The discs can be rotated either clockwise or counterclockwise, and can be rotated with either the left hand or the right hand.

As the discs are rotated, new lenses 86 appear behind openings 94. The magnification power, or diopter rating, of each lens 86 appearing behind openings 94 is identical. Non-prescription reading glasses have the same diopter rating for each lens. As the discs are rotated, the consumer will continue to look at the mirror, until the image appearing in the mirror is clear. At that point, the consumer will note the diopter rating of the lens 86, which appears at the openings 130 (FIG. 2). The lenses and diopter ratings are positioned on the discs 78 to always have the diopter rating for the lens behind opening 94 appear in opening 130. An arrow 134 (FIG. 2) is printed on the vision tester to indicate that the discs 78 are to be rotated, and arrows 136 are printed to point to the diopter ratings. The functions of the arrows are explained in the instructions.

After the consumer determines the appropriate diopter rating for the reading glasses, she will then view all of the glasses on the display rack that have lenses at the appropriate diopter rating. The consumer can then select a pair of reading glasses which the consumer finds to be attractive and comfortable. Mirror 114 is provided to permit the consumer to view the eyeglasses on her face, thereby determining suitability from an appearance standpoint.

As is standard in the art, the eyeglasses 30 on the display rack are segregated by the magnification power, or diopter rating, of the lenses. The consumer will view only that segment of the display rack that contains eyeglasses having the appropriate diopter rating.

The vision tester of this invention provides a convenient and easy-to-use device for permitting a consumer to determine the appropriate magnification for his nonprescription reading glasses. The vision tester can be made an integral part of a display rack for the reading glasses, or it can be placed on a separate support to be used in connection with a display rack for the reading glasses.

Although the vision tester has been shown and described with respect to the rotating discs 78 for varying the lenses, the invention can also be practiced using the other lens-varying devices shown and described in U.S. Pat. No. 5,861,941. Any of these others lens-varying devices can be used in combination with the mirror and placement of the printed vision-testing material of this invention.

Having the printed material at the top of the vision tester permits the lighting in a store to pass directly through the printed material. This makes the printed material brighter and easier to read than would be the case wherein the printed material appears at the back of a vision tester, and light passes only indirectly through it.

Another advantage of the vision tester of this invention is that it is extremely compact. Having a large distance from the printed material to the mirror 104 permits having a short distance from the lenses to the mirror, and thus a shallow display rack, such as that shown at 12. Substantial floor space and depth are required for the display rack and associated vision tester in U.S. Pat. No. 5,861,941. However, it should be understood that the vision tester of this invention will work effectively with the display rack shown in that patent, or with any other display rack, no matter how deep or shallow.

Another advantage of the vision tester of this invention is that when light passes through the transparent or translucent plates and sheet at the top of the vision tester and reflects off the mirror 104, it then passes through the openings 94 at the front of the vision tester. It has been found that this light attracts consumers to the display rack containing the vision tester.

Without further elaboration, the foregoing will so fully illustrate this invention that others may, by applying current or future knowledge, readily adapt the same for use under various conditions of service.

I claim:

1. A vision tester for determining the strength of non-prescription reading glasses required by a consumer, said vision tester comprising a housing, said housing having a front wall, openings in said front wall to permit a consumer to look therethrough, a plurality of magnifying lenses of different diopter ratings selectively positionable behind the openings, a mirror mounted behind said lenses, said mirror being at an angle with respect to said lenses and printed material supported above said mirror, said printed material being reflected in the mirror and viewable by the consumer's looking through said openings and through said lenses to see the printed material reflected off said mirror.

2. The vision tester of claim 1, wherein said mirror is mounted at an obtuse angle with respect to said lenses.

3. The vision tester of claim 1, wherein said printed material lies in a horizontal plane above said mirror.

4. The vision tester of claim 3, wherein said printed material is contained on a sheet positioned between two light-transmitting plates.

5. The vision tester of claim 1, wherein said magnifying lenses are contained in discs, each disc having a plurality of magnifying lenses of different diopter ratings, said discs being rotatable behind said openings, whereby the rotation of said discs brings different magnifying lenses into alignment with said openings.

6. The vision tester of claim 5, wherein said discs are rotationally linked, whereby the rotation of one disc rotates the other.

7. The vision tester of claim 6, wherein said discs are rotationally linked by the engagement of teeth on the circumference of one disc in openings of the other disc.

8. The vision tester of claim 5, wherein the diopter rating for each lens is placed on each disc, said diopter rating being viewable when its corresponding lens is positioned behind said opening.

9. The vision tester of claim 1 and further including an eye shield mounted on said front wall and above said openings.

10. The vision tester of claim 1, wherein the effective length of the distance from said lenses to said mirror to said printed material is approximately 14 inches (35.6cm.).

11. The vision tester of claim 1 and further including a housing for an audio playback device which, upon activation, gives instructions for use of the vision tester.

12. In combination with a display rack for non-prescription reading glasses, a vision tester for determining the strength of the reading glasses required by a consumer, said vision tester comprising a housing, said housing having a front wall, openings in said front wall to permit a consumer to look therethrough, a plurality of magnifying lenses of different diopter ratings selectively positionable behind the openings, a mirror mounted behind said lenses, said mirror being at an angle with respect to said lenses and printed material supported above said mirror, said printed material being reflected in the mirror and viewable by the consumer's looking through said openings and through said lenses to see the printed material reflected off said mirror.

13. The combination of claim 12, wherein the vision tester is mounted on the front of said display rack.

14. The combination of claim 12, wherein said mirror is mounted at an obtuse angle with respect to said lenses.

15. The combination of claim 12, wherein said printed material lies in a horizontal plane above said mirror.

16. The combination of claim 15, wherein said printed material is contained on a sheet positioned between two light-transmitting plates.

17. The combination of claim 12, wherein said magnifying lenses are contained in discs, each disc having a plurality of magnifying lenses of different diopter ratings, said discs being rotatable behind said openings, whereby the rotation of said discs brings different magnifying lenses into alignment with said openings.

18. The combination of claim 12 and further including an eye shield mounted on said front wall and above said openings.

19. The combination of claim 12, wherein the effective length of the distance from said lenses to said mirror to said printed material is approximately 14 inches (35.6cm.).

20. The combination of claim 12 and further including a housing for an audio playback device which, upon activation, gives instructions for use of the vision tester.

* * * * *